US006310003B1

(12) United States Patent
Gries et al.

(10) Patent No.: US 6,310,003 B1

(45) Date of Patent: Oct. 30, 2001

(54) COMPOSITION OF CHEMICALS FOR MANIPULATING THE BEHAVIOR OF THE ORANGE WHEAT BLOSSOM MIDGE, *SITODIPLOSIS MOSELLANA* (GÉHIN)

(75) Inventors: Regine Gries; Gerhard Gries, both of Coqvitlam; Khaskin Grigori, Port Moody; Olfert Owen; Lori-Ann Kaminski, both of Sashatoon, all of (CA)

(73) Assignees: Simon Fraser University, Burnaby; Agriculture and Agri-Food Canada, Saskatoon, both of (CA)

( * ) Notice: Subject to any disclaimer, the term of this patent is extended or adjusted under 35 U.S.C. 154(b) by 0 days.

(21) Appl. No.: 09/725,204

(22) Filed: Nov. 29, 2000

Related U.S. Application Data

(60) Provisional application No. 60/167,890, filed on Nov. 30, 2000.

(51) Int. Cl.[7] .......................... A01N 37/00; C07C 69/00; C07C 67/48; C07C 69/34; C07C 67/30; C07C 67/00

(52) U.S. Cl. .......................... 504/142; 504/307; 560/129; 560/190; 560/191; 560/203; 560/204

(58) Field of Search .................................... 504/142, 307; 560/129, 190, 191, 203, 204

(56) References Cited

PUBLICATIONS

Miller, B. S. and Halton, P. (1961) The damage to wheat kernels caused by the wheat blossom midge (*Sitodiplosis mosellana*). T. Sci. Food Agric. 12:391–398.

Mongrain, D. et al. (1997) Occurrence of the orange wheat blossom midge (Diptera: Cecidomyiidae) in Quebec and its incidence on wheat grain microflora. Phytoprotection 78: 17–22.

Lamb, R. J., et al. (1999) Distribution and seasonal abundance of *Sitodiplosis mosellana* (Diptera: Cecidomyiidae) in spring wheat. Can. Entomol. 131: 387–397.

Knodel, J. and McKay, K. (1998) Results of larval wheat midge survey 1998. NDSU Crop and Pest Report, Aug. 27, 1998.

Barker, P. S. and McKenzie, R. I. H. (1996) Possible sources of resistance to the wheat midge in wheat. Can. J. Plant. Sci. 76: 689–695.

Lamb, R. J., et al. (2000) Resistance to *Sitodiplosis mosellana* (Diptera: Cecidomyiidae) in spring wheat (Gramineae). Can. Entomol. 132: 591–605.

Doane, J. F., et al. (1989) Description of the life stages of Macroglenes penetrans(Kirby) (Hymenoptera: Chalcidoidea, Tperomalidae), a parasitoid of the wheat midge, *Sitodiplosis mosellana* (Gehin) (Diptera: Cecidomyiidae). Can. Entomol. 121: 1041–1048.

Harris, L. (1996) Orange wheat blossom, midge *Sitodiplosis mosellana*. Factsheet. Sustainable Agriculture Facts Growing for tomorrow. Technical information for conservation farmers. Agriculture and Agri–Food Canada –Manitoba, Saskatchewan, Alberta. 6 pp.

Elliott, R. H. (1998a). Evaluation of insecticides for protection of wheat against damage by the wheat midge, *Sitodiplosis mosellana* (Gehin) (Diptera: Cecidomyiidae). Can. Entomol. 120: 615–626.

Elliott, R. H. (1998b) Factors influencing the efficacy and economic returns of aerial sprays against the wheat midge, *Sitodiplosis mosellana* (Gehin) (Diptera: Cecidomyiidae). Can. Entomol. 120: 941–954.

Mukerji, M. K., et al. (1988) Development of sampling designs for egg and larval populations of the wheat midge, *Sitodiplosis mosellana* (Gehin) (Diptera: Cecidomyiidae), in wheat. Can. Entomol. 120: 497–505.

Oakley, J. N., et al. (1994) Forecasting the abundance of orange wheat blossom midge in wheat. Brighton Crop Protection Conference –pests and diseases.

Glogoza, P. A. (1998a) North Dakota field crop insect management guide. NDSU Ext. Pub. E–1143, 50 pp.

Pivnick, K. A. (1993) Response of males to female sex pheromone in the orange wheat blossom midge, *Sitodiplosis mosellana*(Gehin) (Diptera: Cecidomyiidae). J. Chem. Ecol. 91: 1677–1689.

Pivnick, K. A. and Labbe, E. (1992) Emergence and calling rhythms, and mating behaviour of the orange wheat blossom midge, *Sitodiplosis mosellana* (Gehin) (Diptera: Cecidomyiidae). Can. Entomol. 124: 501–507.

Arn, H., et al. (1975) The electroantennographic detector –a selective and sensitive tool in the gas chromatographic analysis of insect phermones. Z. Naturforsch. 30c: 722–725.

Van den Dool, H. and Kratz, P. D. (1963) A generalization of the retention index system including linear temperature programmed gas–liquid partition chromatography. J. Chromatog. 2: 463–471.

Foster, S. P., et al. (1991) Identification of the sex pheromone of the Hessian fly, Mayetiola destructor (Say). Naturwissenschaften 78: 130–131.

Schaus, S. E., et al. (1998) Total synthesis of Muconin by efficient assembly of chiral building blocks. J. Org. Chem. 63: 4876–4877.

Tokunaga, M. et al. (1997) Asymmetric catalysis with water: efficient kinetic resolution of terminal epoxides by means of catalytic hydrolysis, Science 277: 936–938.

Pietruszka, J. et al. (1992) Gas chromatographic enantioseparation of allenes. Tetrahedron Asymmetrie 3: 661–670.

Konig, A., et al. (1992) New, selectively substituted cyclodextrins as stationary phases for the analysis of chiral constituents of essential oils. J. High Resol. Chromatography 15: 367–372.

*Primary Examiner*—Jose'G. Dees
*Assistant Examiner*—Alton Pryor
(74) *Attorney, Agent, or Firm*—Oyen Wiggs Green & Mutala

(57) ABSTRACT

The invention relates to a composition and procedure for manipulating the behavior of the orange wheat blossom midge, *Sitodiplosis mosellana*. More importantly, this invention relates to the preparation and use of 2,7-nonanediyl dibutyrate or stereoisomers thereof for manipulating the behavior of *S. mosellana*.

25 Claims, 9 Drawing Sheets

COMPOSITION OF CHEMICALS FOR MANIPULATING THE BEHAVIOR OF THE ORANGE WHEAT BLOSSOM MIDGE, *SITODIPLOSIS MOSELLANA* (GÉHIN)

The application claims benefit of provisional application No. 60/167,890 filed Nov. 30, 2000.

FIELD OF THE INVENTION

The invention relates to a composition and procedure for manipulating the behaviour of the orange wheat blossom midge, *Sitodiplosis mosellana*. More importantly, this invention relates to the preparation and use of 2,7-nonanediyl dibutyrate or stereoisomers thereof for manipulating the behaviour of *S. mosellana.*

BACKGROUND OF THE INVENTION

The orange wheat blossom midge, *Sitodiplosis mosellana* (SM) (Diptera: Cecidomyiidae), is found around the world wherever wheat is grown. Larvae feed on developing kernels, causing them to shrivel, crack, and deform (1). Grain yield decreases exponentially with the increase in SM larval infestations (2). Damaged kernels are inferior in milling quality and germination capacity (1). SM larval infestations are also correlated with the presence of wheat scab, *Fusarium graminearum,* and glume blotch, *Septoria nordorum* (Berk.), suggesting that SM adults vector fungal spores (3).

Several outbreaks of the SM have been reported in North America since this pest insect became established in Quebec in 1828. In recent years, significant damage to wheat crops occurred in Saskatchewan, Manitoba, Alberta, North Dakota, and Minnesota. In 1983, for example, SM reached epidemic populations in northeastern Saskatchewan, causing revenue losses of >$ 30 million (2). Since then, SM populations have spread across the Northern Plains including most of the wheat-growing area. In 1995, yield losses in Saskatchewan reached 30% in many fields and averaged 15% in the Red River Valley of North Dakota and Minnesota (4). In the same year, total losses exceeded $ 50 million in Manitoba and $ 100 million in Saskatchewan. In North Dakota in 1995, wheat producers lost an estimated 7 million bushels in wheat yield, and $ 30 million in gross revenue due to SM (5).

Cultural, biological and chemical control tactics are employed to manage SM populations. Cultural practices include crop rotation to non-preferred crops, seeding early or late (6), and selecting early maturing varieties. Wheat cultivars resistant to SM would result in long-term reduction of damage (7, 8), but are not yet available. Various biological control agents, such as spiders, mites and hymenopterous parasitoids, prey upon SM populations, but significant crop damage still occurs (9, 10). Insecticides are the current means of controlling SM populations. A single, well-timed application of an insecticide suppresses SM populations, improving crop yield and increasing the farmers' profit (11, 12).

Monitoring of wheat fields is required to identify SM infestations and to take appropriate control measures. Current assessments of SM populations are time-consuming, tedious and not user-friendly. These tactics include captures of adult SM in colored traps, and recording numbers of SM eggs, larvae or adults on heads of wheat (13, 14, 15). Colored traps afford many by-catches which are not readily distinguished from SM. Counts of eggs are laborious and require the use of a stereomicroscope. Counts of adult SM on wheat heads are confounded by the presence of "midge look-a-likes". Uncertain about their SM population assessment, wheat producers often decide to apply unnecessary and costly "insurance sprays". Moreover, ill-timed insecticide applications are not cost-effective, environmentally unacceptable, and adversely affect biological control agents.

Between 1992–3, evidence was presented that female SM produce a sex pheromone to attract male SM (16, 17). This document describes the identification, synthesis and field testing of the SM pheromone.

SUMMARY OF THE INVENTION

Gas chromatographic-electroantennographic detection (GC-EAD) analyses of pheromone gland extract of female orange wheat blossom midge, *Sitodiplosis mosellana* (SM), revealed a single antennally active compound. It was identified as 2,7-nonanediyl dibutyrate. In experiments in wheat fields near Saskatoon and Neilburg, Saskatchewan, Canada, traps baited with stereoisomeric 2,7-nonanediyl dibutyrate or (2S,7S)-2,7-nonanediyl dibutyrate captured significant numbers of male SM.

The essence of the invention is the preparation and use of stereoisomeric 2,7-nonanediyl dibutyrate or (2S,7S)-2,7-nonanediyl dibutyrate for manipulating the behavior of the SM. The invention is directed to the preparation and use of chemicals for manipulating the behavior of SM, said chemical composition comprising (2S,7S)-, (2S,7R)-, (2R,7S)- and (2R,7R)-2,7-nonanediyl dibutyrate.

The chemicals' proportions can cover all possible combinations and ratios. The composition can be contained in, and released from, slow release devices. Pheromone release devices can be held in traps to capture attracted male SM. Pheromone release devices, or micro-encapsulated pheromone, can also be distributed in wheat fields to prevent male SM from locating, and mating with, female SM.

The invention is directed to a composition for manipulating the behaviour of orange wheat blossom midge, *Sitodiplosis mosellana,* said composition comprising: a chemical selected from one or more of the group consisting of: (2S,7S)2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate. The chemicals can be micro-encapsulated.

The invention can include a trap that captures attracted male *S. mosellana,* or a release device, containing a composition according to the invention.

The invention is also directed to a method of preventing male *S. mosellana* from locating, and mating with female *S. mosellana* comprising using a pheromone containing release device, a trap containing a pheromone release device or micro-encapsulated pheromone, said pheromone being a chemical selected from one or more of the group consisting of (2S,7S)-2,7-nonanediyl dibutyrate, (2S,7R)2,7-nonanediyl dibutyrate, (2R,7S)-2,7-nonanediyl dibutyrate and (2R,7R)-2,7-nonanediyl dibutyrate.

The invention also pertains to a process for preparing a mixture of the four stereoisomers of 2,7-nonanediyl dibutyrate which comprises benzylating racemic 4-pentyne-2-ol to yield 2-O-benzyl-4-pentyne, treating 2-O-benzyl-4-pentyne with butyl lithium and butylene epoxide to yield 2-O-benzyl-4-nonyne-2,7-diol, hydrogenating 2-O-benzyl-4-nonyne-2,7-diol to yield 2,7-nonanediol and esterifying 2,7 nonanediol to yield 2,7-nonanediyl dibutyrate.

The invention also pertains to a process for preparing four optically active stereoisomers of 2,7-nonanediyl dibutyrate comprising: (a) coupling S-propylene oxide with Grignard reagent derived from 5-bromo-1-pentene to yield (2S)-8-octen-2ol, oxidizing (2S)-8-octen-2-ol with m-chloroperoxybenzoic acid to yield (7S)-1,2-epoxy-7-hydroxyoctane, kinetically resolving (7S)-1,2-epoxy-7-hydroxyoctane with (R,R)-N,N-bis(3,5-di-tert-butylsalicylidene)-1,2-cyclohexanediaminocobalt (II) and water to yield (2R,7S)-1,2-epoxy-7-hydroxyoctane, opening the epoxy ring of (2R,7S)1,2-epoxy-7-hydroxyoctane with methylmagnesium bromide in the presence of CuI to yield (2S,7S)-2,7-nonanediol, esterifying (2S,7S)-2,7-nonanediol to yield (2S,7S)-2,7-nonanediyl dibutyrate; and (b) when the remaining three stereoisomers are desired, synthesizing respective epoxide intermediates from (S)- or (R)-propylene oxide and 5bromo-1-pentene, kinetically resolving these intermediates, opening their epoxy rings and esterifying the diols.

The invention is also directed to a method of alleviating wheat damage in a wheat field caused by *Sitodiplosis mosellana* which comprises deploying in the field a release device or micro-encapsulation containing a chemical selected from one or more of the group consisting of: (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

The invention also pertains to a method of diagnosing the population density of *Sitodiplosis mosellana* in a wheat field which comprises deploying in the field a trap baited with a release device containing a chemical selected from one or more of the group consisting of: (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

DRAWINGS

Drawings illustrate specific embodiments of the invention, but should not be construed as restricting the spirit or scope of the invention in any way:

DETAILED DESCRIPTION OF INVENTION

Analysis of Pheromone Extract of Female *S. mosellana*

Aliquots of 5–10 female equivalents (FE) of abdominal tip extract were analyzed by coupled gas chromatographic-electroantennographic detection (GC-EAD)(18,19). These analyses revealed a single candidate pheromone (CP) that elicited a response from male SM antenna (FIG. 1).

Figure 1:
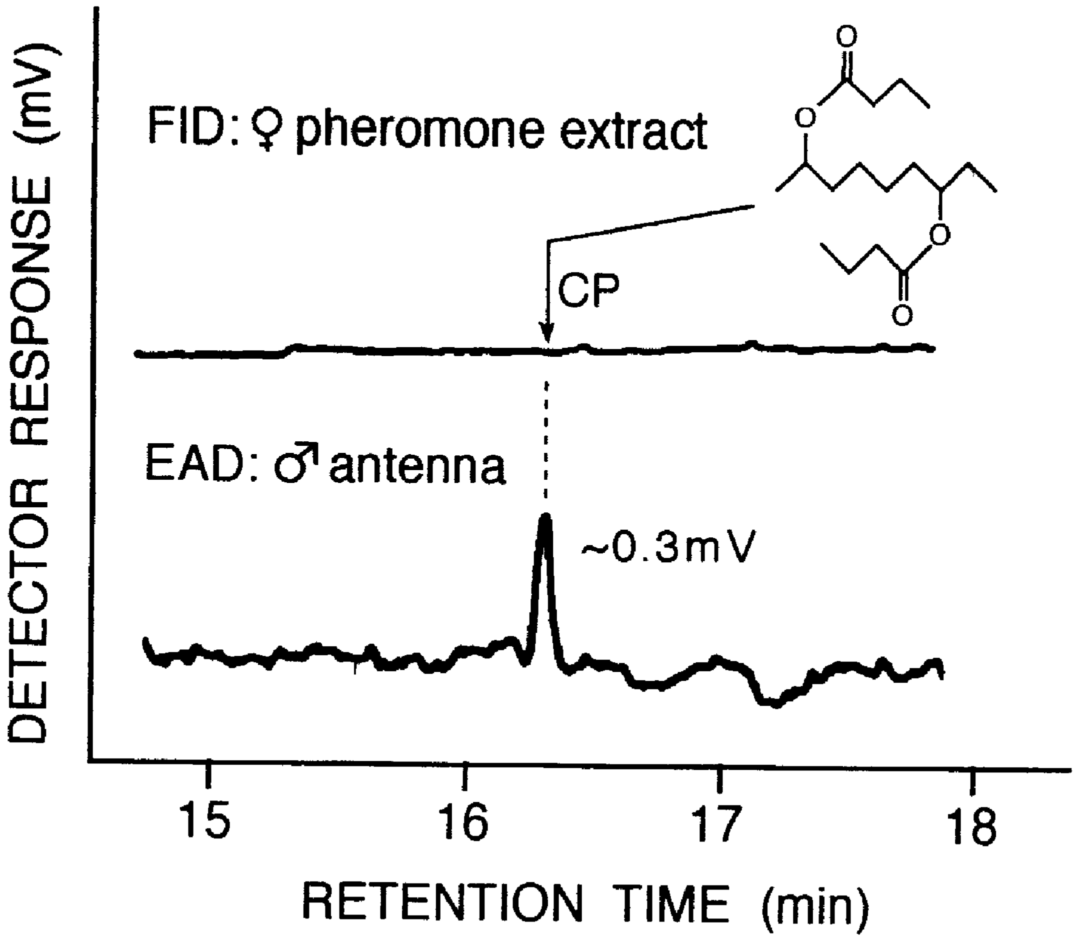
FIG. 1 illustrates flame ionization detector (FID) and electroantennographic detector (EAD: male *S. mosellana* antenna) responses to one female equivalent of female *S. mosellana* pheromone extract. CP=Candidate Pheromone.

FIG. 1 illustrates flame ionization detector (FID) and electroantennographic detector (EAD: male *S. mosellana* antenna) responses to one equivalent of female *S. mosellana* pheromone extract. Chromatography: Hewlett Packard (HP) gas chromatograph (GC) 5890 equipped with a fused silica column (30 m×0.25 mm ID) coated with DB-5 (J & W, Scientific, Folsom Calif.); splittless injection, temperature of injection port 240° C. and FID 250° C.; temperature program: 50° C. (1 min), 25° C./min to 100° C., then 10° C. to 280° C. Retention indices (20) of the candidate pheromone (CP) on columns coated with DB-5, DB-210, DB-23 and SP-1000 were 1863, 2343, 2348 and 2272, respectively.

Hydrogenation of pheromone gland extract (50 FE) followed by renewed GC-EAD analysis did not alter the antennal response to CP, indicative that it had no double bond(s). A very weak mass spectrum of CP in a highly concentrated extract (>200 FE) revealed the fragmentation ion m/z 89, indicative of a butyric ester. However, inter-column differences of CP retention indices (21) were about 2-times greater than those of monobutyric esters.

Taking into account: 1) that CP was likely a dibutyric ester with no more than 9 carbon atoms in the molecule chain, and 2) that secondary tridecen-2-yl and tridecadien-2-yl acetates are known to attract cecidomyiid midges (22, 23), we hypothesized that CP may be 2,7-octanediyl dibutyrate or a 2,8-nonanediyl dibutyrate. The latter had retention indices on all analytical columns similar to those of CP. The correct molecular structure of CP was then approximated by synthesizing various dibutyric and diisobutyric esters, with one ester group conservatively kept in position C2, whereas the second ester group was placed in C6, C7 and C9. Synthetic 2,7-nonanediyl dibutyrate and CP had identical retention and comparable EAD characteristics on all four analytical columns. Moreover, the mass spectrum of synthetic 2,7-nonanediyl dibutyrate (FIG. 2) greatly resembled the weak mass spectrum of CP, further confirming the structural assignment.

Figure 2:
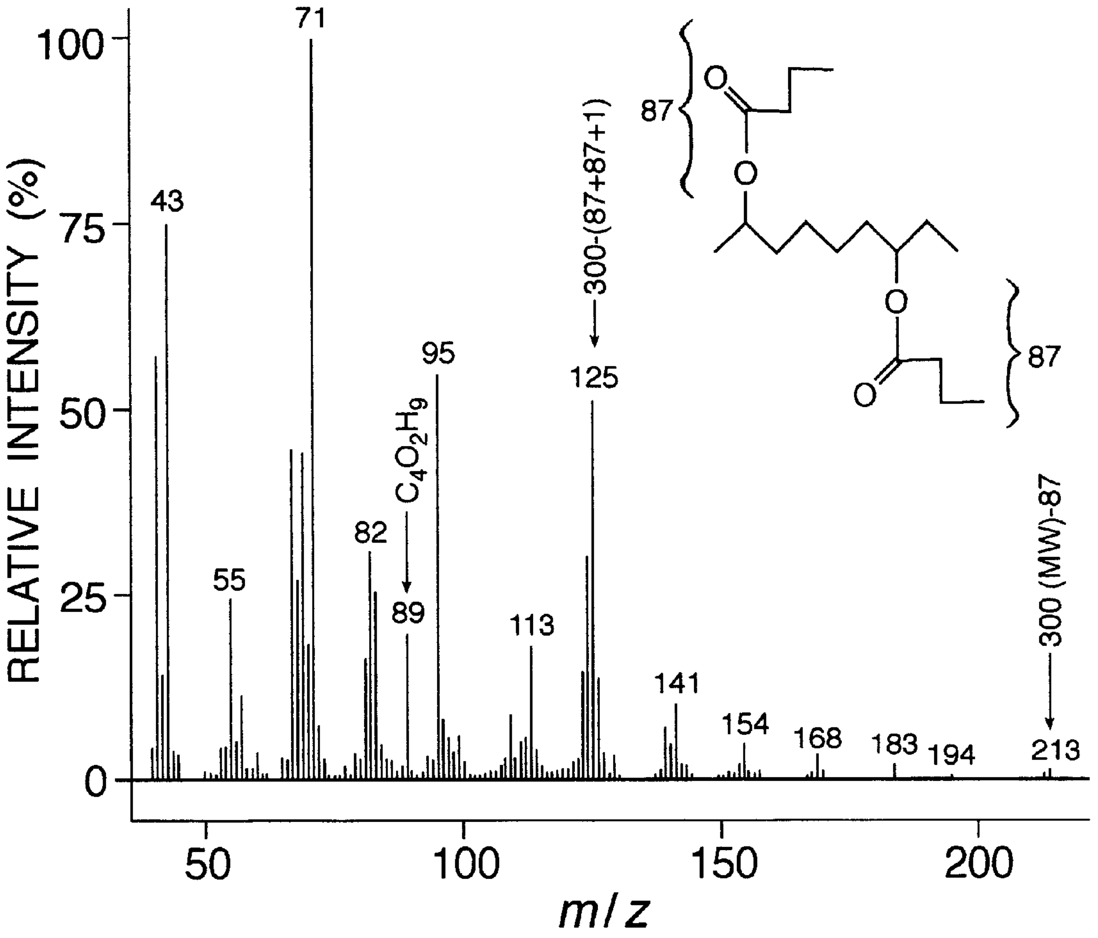
FIG. 2 illustrates the mass spectrum of 2,7-nonanediyl dibutyrate, the pheromone of the orange wheat blossom midge, *S. mosellana*.

FIG. 2 illustrates the mass spectrum of synthetic stereoisomeric 2,7-nonanediyl dibutyrate. Varian 2000 GC-tandem mass spectrometer (MS/MS).

2,7-Nonanediyl dibutyrate was synthesized starting from racemic 4-pentyne-2-ol (1). Compound 1 was benzylated resulting in benzyloxy acetylene (2;92% yield), which was treated with butyl lithium at −70° C., and then warmed-up in the presence of butylene epoxide to give 2-O-benzyl-4-nonyne-2,7-diol (3; 55% yield). Hydrogenation of 3 in the presence of 10% Pd/C afforded 2,7-nonanediol (4; 93% yield). The diol 4 was then esterified to 2,7-nonanediyl dibutyrate (5; 98% yield); analytically calculated for $C_{17}H_{32}O_4$: C, 67.96; H, 10.74; found: C, 68.07; H, 10.85. $^1H$ NMR (Bruker AMX-400 spectrometer at 400.13 MHz, $CDCl_3$) δ: 4.88 (1H, sextet), 4.80 (1H, quintet), 2.25 (4H, q), 1.64 (4H, m.), 1.52 (6H, m.), 1.29 (4H, m), 1.19 (3H, d.), 0.92 (6H, two unresolved t.), 0.88 (3H, t.) (FIG. 3).

Figure 3:
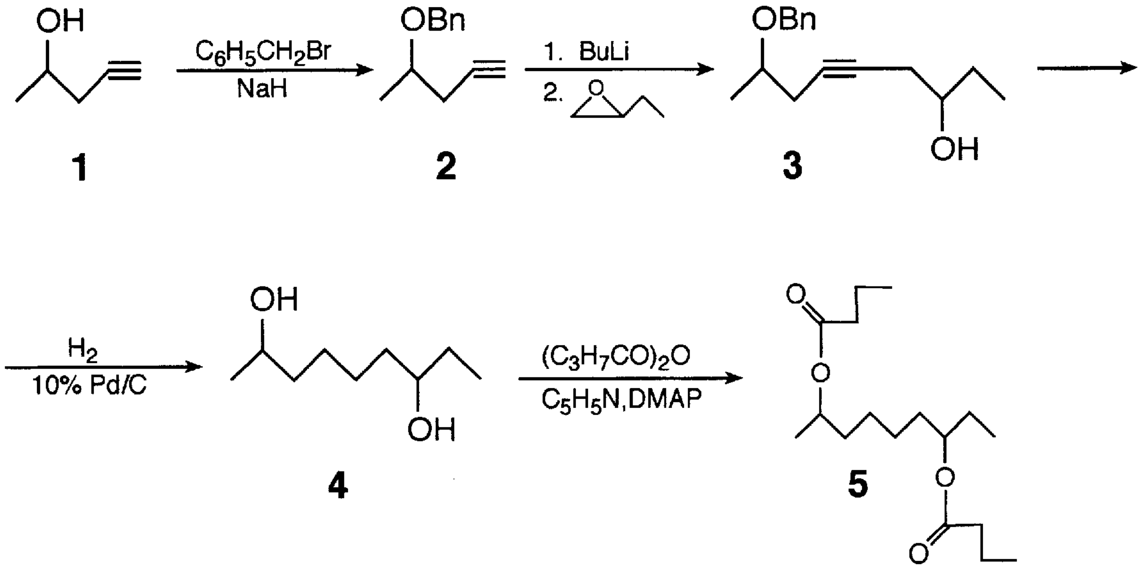
FIG. 3 illustrates the scheme for the synthesis of stereoisometric 2,7-nonanediyl dibutyrate.

FIG. 3 illustrates the scheme for the 5-step synthesis of stereoisomeric 2,7-nonanediyl dibutyrate.

Figure 4:
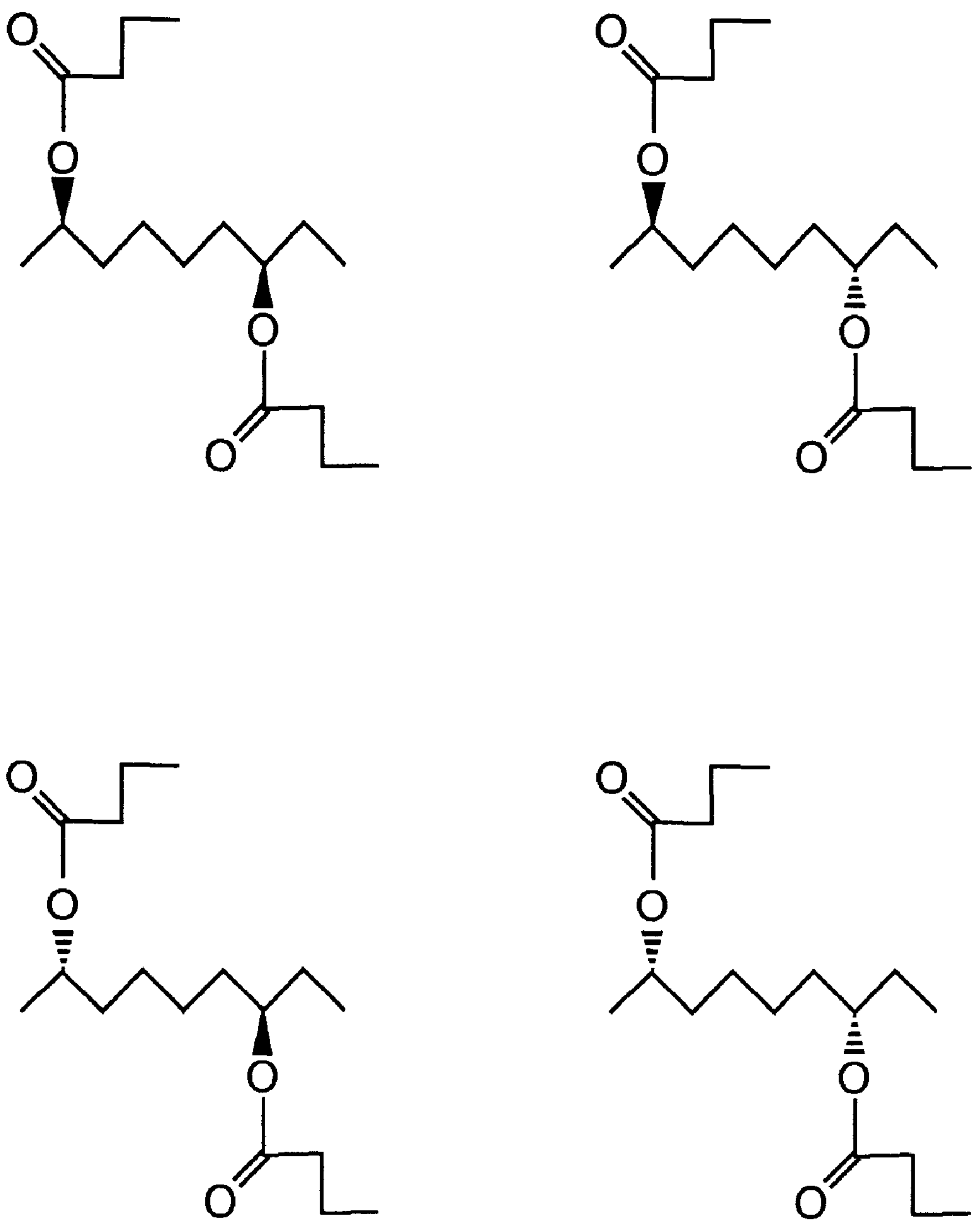
FIG. 4 illustrates the four stereoisomers of 2,7-nonanediyl dibutyrate.

There are four optical isomers (stereoisomers) of 2,7-nonanediyl dibutyrate (FIG. 4).

FIG. 4 illustrates the molecular structure of the four stereoisomers of 2,7-nonanediyl dibutyrate.

Following field experiments, the absolute configuration of the attractive stereoisomer was determined to be (2S,7S)-2,7-nonanediyl dibutyrate through stereospecific syntheses (FIG. 5) and chromatographic analyses of all 4 individual stereoisomers.

Figure 5:
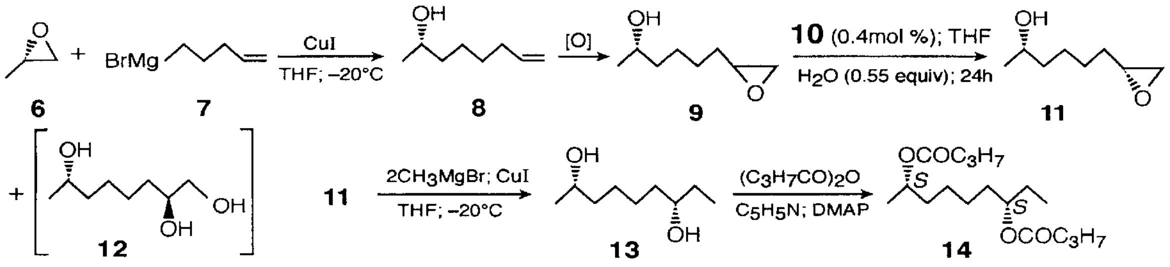
FIG. 5 illustrates the scheme for the synthesis of (2S,7S)-2,7-nonanediyl dibutyrate.

FIG. 5 illustrates the scheme for the synthesis of field-active (2S,7S)2,7-nonanediyl dibutyrate (14): S-propylene oxide (6) (Fluka Chemika-Biochemika, Buchs, Switzerland) was coupled at −20° C. with Grignard reagent 7 in the presence of 0.1 equivalents of a CuI catalyst. Resulting (2S)-8-octen-2-ol (8) was oxidized by m-chloroperoxybenzoic acid (Aldrich Chemical Co.) to the terminal epoxide 9. Hydrolytic kinetic resolution of 9 with Co(II) salen (Jacobsen's) catalyst (R,R)N,N'-bis(3,5-di-tert-butylsalicylidene)-1,2-cyclohexanediaminoc (10) (Aldrich Chemical Co.) (24, 25) afforded 2(R),7(S)-1,2-epoxy-7-hydroxyoctane (11), which was separated from unwanted 1,2(S),7(S)-octanetriol (12) by silica flash chromatography [hexane: ether (1:1), then ether as eluents]. Ring opening of 11 with excess of methylmagnesium bromide (Aldrich Chemical Co.) and catalytic amounts of CuI yielded (2S, 7S)-2,7-nonanediol (13) which was esterified to (2S,7S)-2, 7-nonanediol dibutyrate [14; 77% enantiomeric excess (ee) as determined by chiral GC; 37% overall yield]. GC-MS and NMR data of 14 were consistent with those of 5 (FIG. 4). The remaining 3 stereoisomers of diester 5 were synthesized from (S)- or (R)-propylene oxide (Fluka Chemika-Biochemika) and 5-bromo-pentene (Aldrich Chemical Co.), again by hydrolytic kinetic resolution of terminal epoxide intermediates, with ee of end products ranging between 73–85%.

Figure 6:
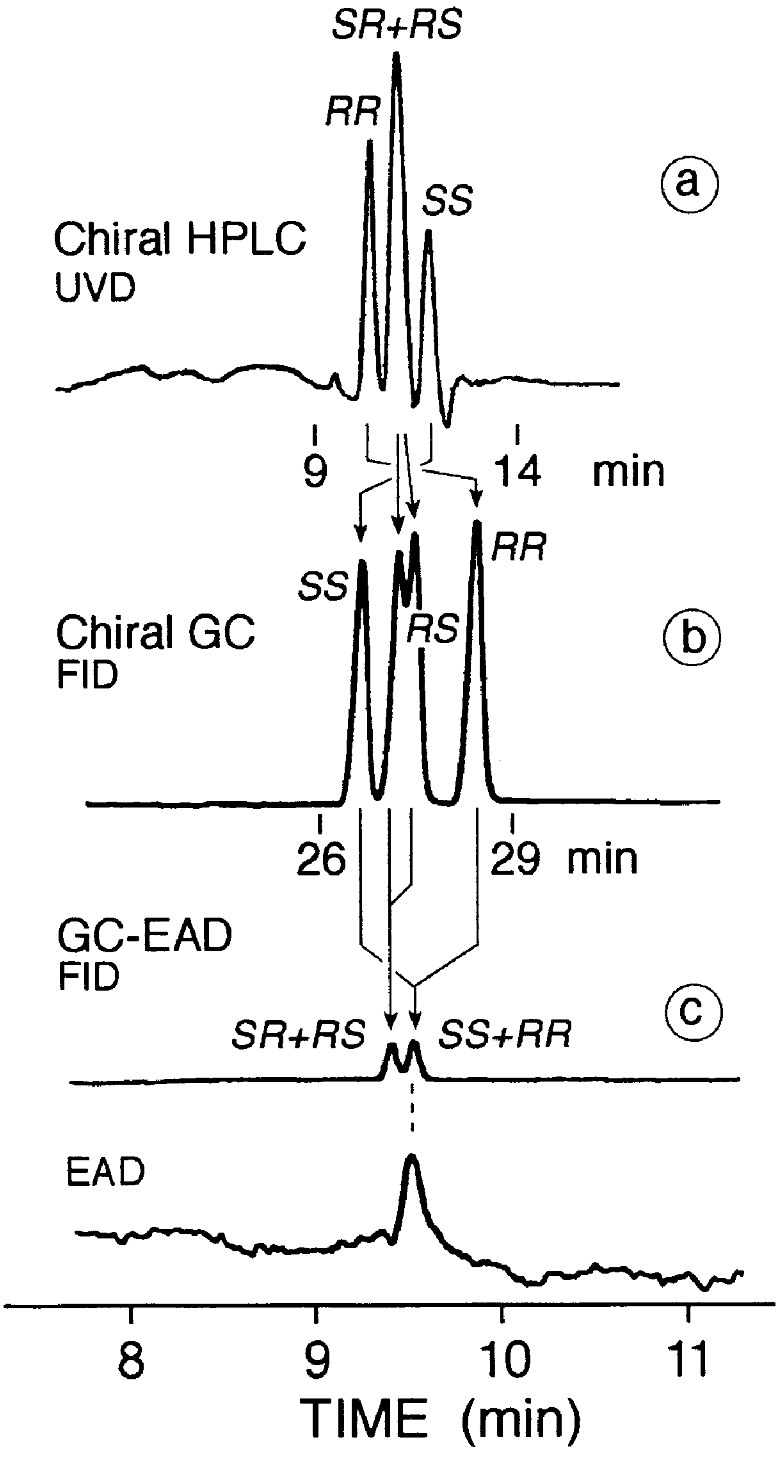
FIG. 6 illustrates the separation of the four stereoisomers of 2,7-nonanediyl dibutyrate by chromatographic techniques.

The SS-stereoisomer had chromatographic characteristics identical to the late eluting stereoisomer of synthetic mosellin on the chiral HPLC column (FIG. 6), and to the first eluting stereoisomer on the chiral GC column (FIG. 6). It also elicited the strongest antennal response.

FIG. 6 illustrates the separation of stereoisomers of 2,7-nonanediyl dibutyrate by chromatographic techniques. a) High performance liquid chromatography (HPLC): Waters LC 626 high-performance liquid chromatograph equipped with a Waters 486 variable wavelength UV visible detector (UVD) set to 200 nm, a Water 746 Data Module and a Chiralpak AD column [250×4.6 mm (L.×I.D.); Chiral Technologies Inc., Exton, Pa. 19341]; solvent system: 99% hexane plus 1% 2-propanol with a flow rate of 0.8 ml/min.) Gas chromatography (GC): HP5890 GC equipped with a custom-made chiral fused silica column coated with a 1:1 mixture of heptakis(2,6-di-O-methyl-3-O-pentyl)-β-cyclodextrin and OV-1701 (26, 27); splittless injection, temperature of injection port and FID as in a); temperature program: 145° C. isothermal. c) FID and EAD (male *S. mosellana* antenna) responses to synthetic stereoisomers of 2,7-nonanediyl dibutyrate; chromatography: HP5890 GC equipped with a fused silica column coated with DB-210, splittless injection, temperature of injection port and FID as in b); temperature program: 180° C. isothermal.

Attraction of Male *S. mosellana* to Synthetic Test Chemicals

Field experiments with synthetic chemicals were carried out in wheat fields in Saskatchewan, employing a complete randomized design. Pherocon wing traps were placed at 20 m intervals ~20 cm above ground and baited with Whatman #1 filter paper impregnated with HPLC fractionated test chemicals in solvent or with a solvent control.

EXAMPLE #1

Figure 7:
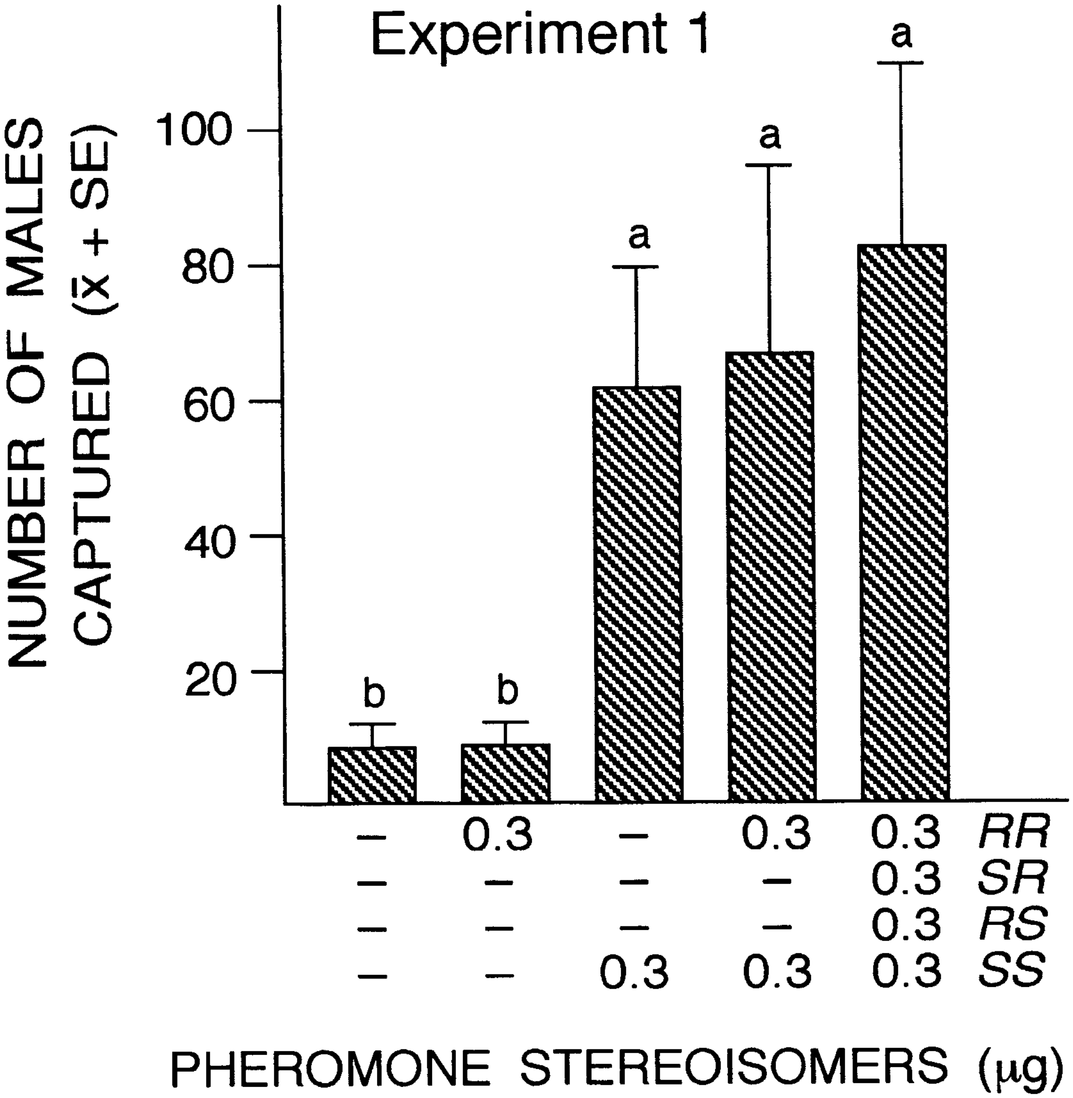
FIG. 7 illustrates graphical data of captures of male *S. mosellana* in Pherocon wing traps baited with stereoisomers of 2,7-nonanediyl dibutyrate.

In experiment 1, traps baited with (2S,7S)-2,7-nonanediyl dibutyrate or stereoisomeric 2,7-nonanediol dibutyrate captured significant numbers of male *S. mosellana* (FIG. 7).

FIG. 7 illustrates graphical data of captures of male *S. mosellana* in Pherocon wing traps baited with stereoisomers of 2,7-nonanediyl dibutyrate. Wheat fields near Saskatoon, Saskatchewan, Canada; Jul. 22–28, 1999; 3 replicates. Bars with the same letter superscript are not significantly different; Kruskal-Wallis analysis of variance by ranks (28) followed by comparison of means (Student-Newman-Keuls test), $P<0.05$.

EXAMPLE #2

Figure 8:
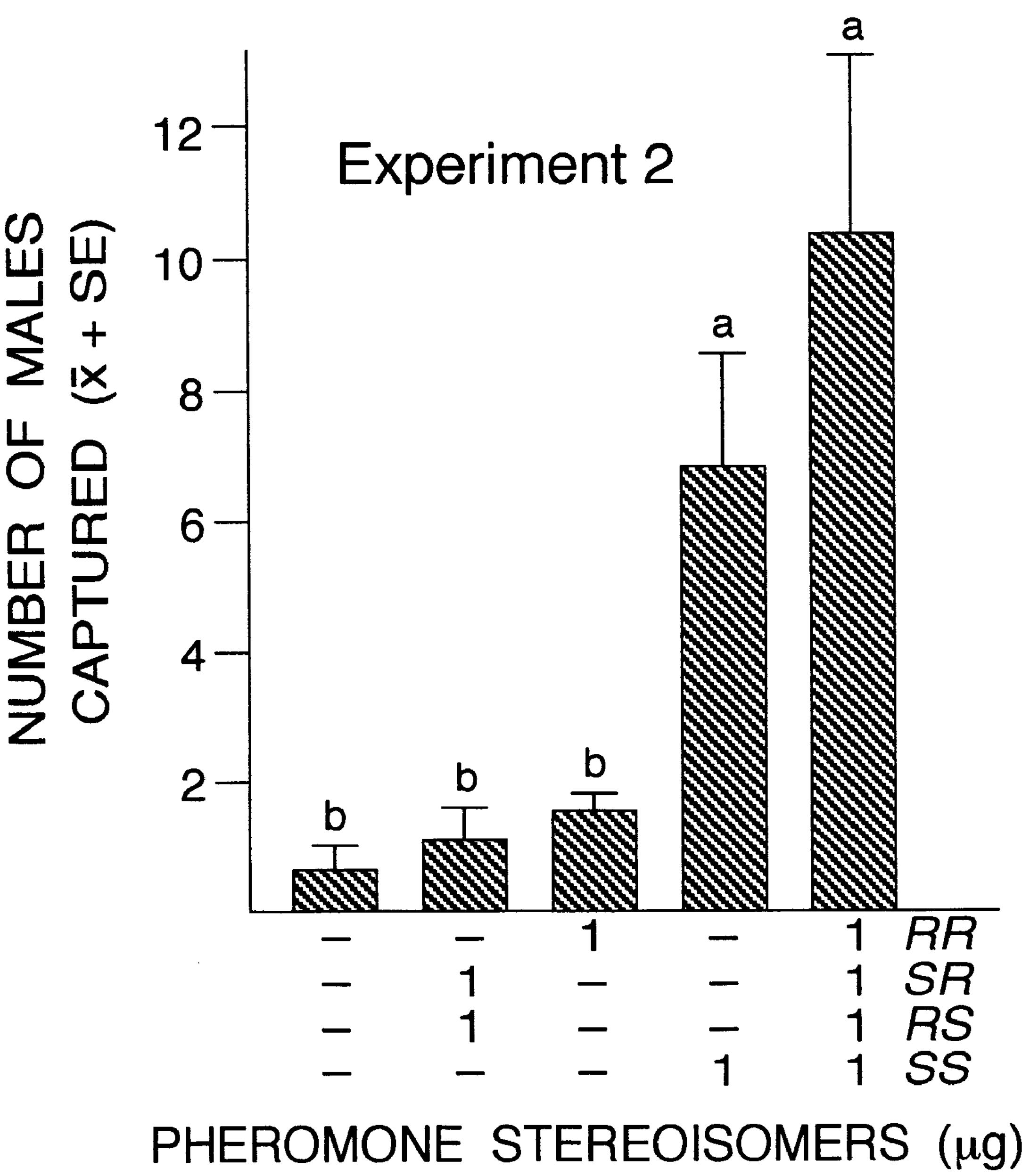
FIG. 8 illustrates graphical data of captures of male *S. mosellana* in Pherocon wing traps baited with stereoisomers of 2,7-nonanediyl dibutyrate.

Also in field experiment 2, traps baited with (2S,7S)-2, 7-nonanediyl dibutyrate alone or in combination with other stereoisomers captured significant numbers of male *S. mosellana* (FIG. 8).

FIG. 8 illustrates graphical data of captures of male *S. mosellana* in traps baited with stereoisomers of 2,7-nonanediyl dibutyrate. Wheat field near Neilburg, Saskatchewan, Canada; Aug. 1–6, 1999; 10 replicates. Bars with the same letter superscript are not significantly different; Kruskal-Wallis analysis of variance by ranks (28) followed by comparison of means (Student-Newman-Keuls test), $P<0.05$.

EXAMPLE #3

Figure 9:
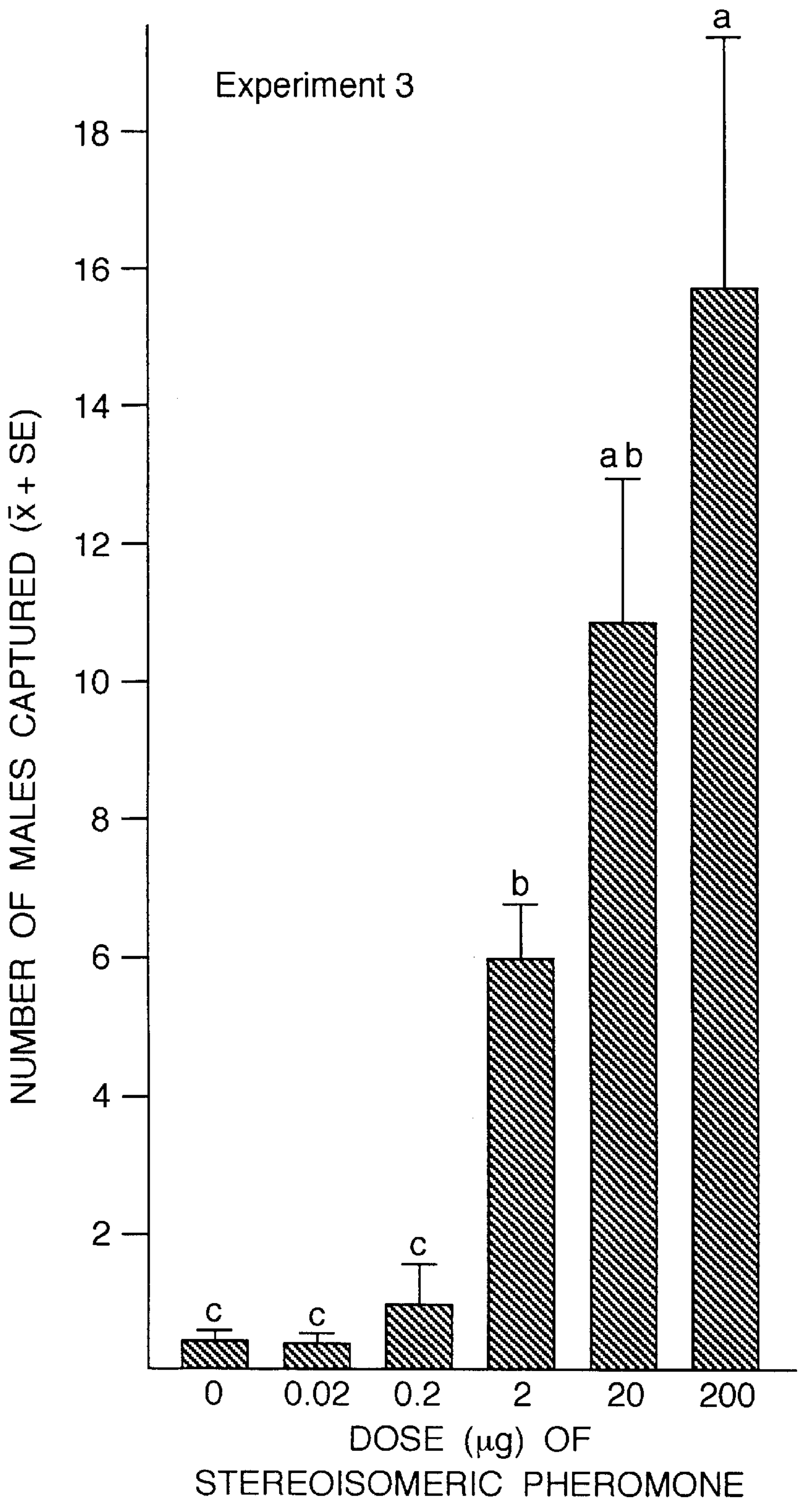
FIG. 9 illustrates graphical data of captures of male *S. mosellana* in Pherocon wing traps baited with increasing amounts of stereoisomeric 2,7-nonanediyl dibutyrate.

In experiment 3, increasing amounts of stereoisomeric 2,7-nonanediyl dibutyrate resulted in increasing numbers of trap captured male *S. mosellana* (FIG. 9).

FIG. 9 illustrates graphical data of captures of *S. mosellana* in Pherocon wing traps baited with increasing amounts of synthetic stereoisomeric 2,7-nonanediyl dibutyrate. Wheat field near Neilburg, Saskatchewan, Canada, Aug. 2–6, 1999; 10 replicates. Bars with the same letter superscript are not significantly different; Kruskal-Wallis analysis of variance by ranks (26) followed by comparison of means (Student-Newman-Keuls test), $P<0.05$.

All compounds may become part of a commercial lure (formulation) for pheromone-based monitoring, manipulating and/or control of SM populations. As will be apparent to those skilled in the art in light of the foregoing disclosure, many alterations and modifications are possible in the practice of this invention without departing from the spirit or scope thereof. Accordingly, the scope of the invention is to be construed in accordance with the substance defined by the following claims.

REFERENCES AND NOTES

1. Miller, B. S. and Halton, P. (1961) The damage to wheat kernels caused by the wheat blossom midge (*Sitodiplosis mosellana*). T. Sci. Food Agric. 12: 391–398.
2. Olfert, O. O., Mukerji, M. K. and Doane, J. F. (1985) Relationship between infestation levels and yield loss caused by wheat midge, *Sitodiplosis mosellana* (Géhin) (Diptera: Cecidomyiidae), in spring wheat in Saskatchewan. Can. Entomol. 117: 593–598.
3. Mongrain, D., Couture, L., Dubuc, J.-P., and Comeau, A. (1997) Occurrence of the orange wheat blossom midge (Diptera: Cecidomyiidae) in Quebec and its incidence on wheat grain microflora. Phytoprotection 78: 17–22.
4. Lamb, R. J., Wise, I. L., OLfert, O. O., Gavloski, J., and Barker, P. S. (1999) Distribution and seasonal abundance of *Sitodiplosis mosellana* (Géhin) (Diptera: Cecidomyiidae) in spring wheat. Can. Entomol. 131: 387–397.
5. McKay, K. and Glogoza, P., personal communication.
6. Knodel, J. J. (1998) Results of larval wheat midge survey 1998. NDSU Crop and Pest Report, Aug. 27, 1998.
7. Barker, P. S. and McKenzie, R. I. H. (1996) Possible sources of resistance to the orange wheat blossom midge in wheat. Can. J. Plant. Sci. 76: 689–695.

8. Lamb, R. J. (1998) Crop resistance for wheat midge in spring wheat. Abstract. Entomol Soc. Manitoba Inc. Pest Control: Prospects for Innovation, Pressures for Change. Oct. 16–17, 1998.

9. Doane, J. F., DeClerck-Floate, R. and Arthur, A. P. (1989). Description of the life stages of *Macroglenes penetrans* (Kirby) (Hymenoptera: Chalcidoidea, Pteromalidae), a parasitoid of the wheat midge, *Sitodiplosis mosellana* (Géhin) (Diptera: Cecidomyiidae). Can. Entomol. 121: 1041–1048.

10. Harris, L. (1996) Orange wheat blossom midge *Sitodiplosis mosellana.* Factsheet. Sustainable Agriculture Facts Growing for tomorrow. Technical information for conservation farmers. Agriculture and Agri-Food Canada—Manitoba, Saskatchewan, Alberta. 6 pp.

11. Elliott, R. H. (1998*a*) Evaluation of insecticides for protection of wheat against damage by the wheat midge, *Sitodiplosis mosellana* (Géhin) (Diptera: Cecidomyiidae). Can. Entomol. 120: 615–626.

12. Elliott, R. H. (1998*b*) Factors influencing the efficacy and economic returns of aerial sprays against the wheat midge, *Sitodiplosis mosellana* (Géhin) (Diptera: Cecidomyiidae). Can. Entomol. 120: 941–954.

13. Murkerji, M. K., Olfert, O. O., and Doane, J. F. (1988) Development of sampling designs for egg and larval populations of the wheat midge, *Sitodiplosis mosellana* (Géhin) (Diptera: Cecidomyiidae) in wheat. Can. Entomol. 120: 497–505.

14. Oakley, J. N., Green, D. I., Jones, A. E., Kilpatrik, J. B., and Young, J. E. B. (1994) Forecasting the abundance of orange wheat blossom midge in wheat. Brighton Crop Protection Conference—pests and diseases.

15. Glogoza, P. A. (1998*a*) North Dakota field crop insect management guide. NDSU Ext. Pub. E-1143, 50 pp.

16. Pivnick, K. A. (1993) Response of males to female sex pheromone in the orange wheat blossom midge, *Sitodiplosis mosellana* (Géhin) (Diptera: Cecidomyiidae). J. Chem. Ecol. 91: 1677–1689.

17. Pivnick, K. A. and E. Labbe (1992) Emergence and calling rhythms, and mating behaviour of the orange wheat blossom midge, *Sitodiplosis mosellana* (Géhin) (Diptera: Cecidomyiidae). Can. Entomol. 124: 501–507.

18. Arn, H., Städler, E., and Rauscher, S. (1975) The electroantennographic detector—a selective and sensitive tool in the gas chromatographic analysis of insect pheromones. Z Naturforsch. 30c: 722–725.

19. GC-EAD analyses employed a Hewlett-Packard (HP) 5890 gas chromatograph fitted with a fused silica column (30 m×0.25 or 0.32 mm ID) coated with either DB-210, DB-5, DB-23 (J & W Scientific, Folsom, Calif. 95630) or SP-1000 (Supelco, Bellefonte, Pa.).

20. Van den Dool, H., and Kratz, P. D. (1963) A generalization of the retention index system including linear temperature programmed gas-liquid partition chromatography. J Chromatography 2: 463471.

21. Inter-column differences in retention indices of the antennally active compound were (e. g.): DB-23 to DB-5, 485; DB-5 to DB-210, 480; DB-23 to DB-210, 5; DB-5 to SP 1000, 409).

22. Foster, S. P., Harris, M. O., and Millar, J. G. (1991) Identification of the sex pheromone of the Hessian fly, *Mayetiola destructor* (Say). Naturwissenschaften 78: 130–131.

23. Gries et al., unpublished.

24. Schaus, S. E., Branalt, J., and Jacobsen, E. N. (1998) Total synthesis of Muconin by efficient assembly of chiral building blocks. J. Org. Chem. 63: 48764877.

25. Tokunaga, M., Farrow, J. F., Kakuichi, F., and Jacobsen. E. N. (1997) Asymmetric catalysis with water: Efficient kinetic resolution of terminal epoxides by means of catalytic hydrolysis. Science 277: 936–938.

26. Pietruska J, Hochmuth D H, Gehrke B, Icheln D, Runge T, and König W. (1992) Gas chromatographic enantioseparation of allenes. Tetrahedron Asymmetrie 3: 661–670.

27. König, W. A., Gehrke, B., Icheln, D., Evers, P., Donnecke, J., and Wang, W. (1992) New selectively substituted cyclodextrins as stationary phases for the analysis of chiral constituents of essential oils. J. High Resol Chromatography 15: 367–372.

28. Zar, J. H. 1984. Biostatistical Analysis. Prentice-Hall, Englewood Cliffs, N.J., 718 pp.

We claim:

1. A composition for manipulating the behaviour of orange wheat blossom midge, *Sitodiplosis mosellana,* said composition comprising: a chemical selected from one or more of the group consisting of: (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

2. A composition as claimed in claim 1 wherein the chemical comprises (2S,7S)-2,7-nonanediyl dibutyrate.

3. A composition as claimed in claim 1 wherein the chemical comprises (2S,7R)-2,7-nonanediyl dibutyrate.

4. A composition as claimed in claim 1 wherein the chemical comprises (2R,7S)-2,7-nonanediyl dibutyrate.

5. A composition as claimed in claim 1 wherein the chemical comprises (2R,7R)-2,7-nonanediyl dibutyrate.

6. A composition as claimed in claim 1 wherein the chemicals are micro-encapsulated.

7. A composition as claimed in claim 2 wherein the chemicals are micro-encapsulated.

8. A composition as claimed in claim 3 wherein the chemicals are micro-encapsulated.

9. A composition as claimed in claim 4 wherein the chemicals are micro-encapsulated.

10. A composition as claimed in claim 5 wherein the chemicals are micro-encapsulated.

11. A trap that captures attracted male *Sitodiplosis mosellana,* containing a composition as claimed in claim 1.

12. A trap that captures attracted male *Sitodiplosis mosellana,* containing a composition as claimed in claim 2.

13. A trap that captures attracted male *Sitodiplosis mosellana,* containing a composition as claimed in claim 3.

14. A trap that captures attracted male *Sitodiplosis mosellana,* containing a composition as claimed in claim 4.

15. A trap that captures attracted male *Sitodiplosis mosellana,* containing a composition as claimed in claim 5.

16. A release device containing a composition as claimed in claim 1.

17. A release device containing a composition as claimed in claim 2.

18. A release device containing a composition as claimed in claim 3.

19. A release device containing a composition as claimed in claim 4.

20. A release device containing a composition as claimed in claim 5.

21. A method of preventing male *Sitodiplosis mosellana* from locating, and mating with female *S. mosellana* comprising deploying in a wheat field a pheromone containing release device, or micro-encapsulated pheromone, said pheromone being a chemical selected from one or more of the group consisting of (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

22. A synthetic process for preparing a mixture containing the four stereoisomers of 2,7-nonanediyl dibutyrate which comprises benzylating racemic 4-pentyne-2-ol to yield 2-O-benzyl-4-pentyne, treating 2-O-benzyl-4-pentyne with butyl lithium and butylene epoxide to yield 2-O-benzyl-4-nonyne-2,7-diol, hydrogenating 2-O-benzyl-4-nonyne-2,7-diol to yield 2,7-nonanediol and esterifying 2,7-nonanediol to yield 2,7-nonanediyl dibutyrate.

23. A synthetic process for preparing four optically active stereoisomers of 2,7-nonanediol dibutyrate comprising:

(a) coupling S-propylene oxide with Grignard reagent derived from 5-bromo-1-pentene to yield (2S)-8-octen-2-ol, oxidizing (2S)-8-octen-2-ol with m-chloroperoxybenzoic acid to yield (7S)-1,2-epoxy-7-hydroxyoctane, kinetically resolving (7S)-1,2-epoxy-7-hydroxyoctane with (R,R)-N,N-bis(3,5-di-tert-butylsalicylidene)-1,2-cyclohexanediaminocobalt (II) and water to yield (2R,7S)-1,2-epoxy-7-hydroxyoctane, opening the epoxy ring of (2R,7S)-1,2-epoxy-7-hydroxyoctane with methylmagnesium bromide in the presence of CuI to yield (2S,7S)-2,7-nonanediol, esterifying (2S,7S)-2,7-nonanediol to yield (2S,7S)-2,7-nonanediyl dibutyrate; and (b) when either of the remaining three stereoisomers is desired, synthesizing respective epoxy intermediates from (S)- or (R)-propylene oxide and 5-bromo 1-pentene, kinetically resolving these intermediates, opening their epoxy rings and esterifying the diols.

24. A method of alleviating wheat damage in a wheat field caused by *Sitodiplosis mosellana* which comprises deploying in the field release devices or micro-encapsulation containing a chemical selected from one or more of the group consisting of: (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

25. A method of diagnosing the population density of *Sitodiplosis mosellana* in a wheat field which comprises deploying in the field traps baited with a release device containing a chemical selected from one or more of the group consisting of: (2S,7S)-2,7-nonanediyl dibutyrate, (2S,7R)-2,7-nonanediyl dibutyrate, (2R,7S)-2,7-nonanediyl dibutyrate and (2R,7R)-2,7-nonanediyl dibutyrate.

* * * * *